United States Patent [19]

Crooks

[11] 4,210,558
[45] Jul. 1, 1980

[54] REACTIVATION OF SPENT COPPER CONTAINING HYDROCYANATION CATALYSTS

[75] Inventor: Graham R. Crooks, Wilton, England

[73] Assignee: Imperial Chemical Industries Limited, London, England

[21] Appl. No.: 955,246

[22] Filed: Oct. 27, 1978

[30] Foreign Application Priority Data

Nov. 7, 1977 [GB] United Kingdom ............... 46211/77

[51] Int. Cl.² .................... B01J 27/32; C07C 120/02
[52] U.S. Cl. .................................. 252/415; 260/465.3
[58] Field of Search ............................ 252/415, 429 R; 260/465.3

[56] References Cited

U.S. PATENT DOCUMENTS

| 2,553,008 | 5/1951 | Sager | 260/465.3 |
| 2,920,098 | 1/1960 | Burrus et al. | 252/429 R |
| 3,114,764 | 12/1963 | Rowbottom | 252/429 R |
| 3,344,084 | 9/1967 | Leland | 252/415 |

FOREIGN PATENT DOCUMENTS

| 1429169 | 3/1976 | United Kingdom . |
| 1429651 | 3/1976 | United Kingdom . |
| 1482909 | 8/1977 | United Kingdom . |

Primary Examiner—P. E. Konopka
Attorney, Agent, or Firm—Cushman, Darby & Cushman

[57] ABSTRACT

Spent copper halide hydrocyanation catalysts are reactivated by treating with hydrogen halide. The process is particularly applicable to the hydrocyanation of butadiene to 3-pentenenitrile in the presence of a copper halide catalyst.

7 Claims, 1 Drawing Figure

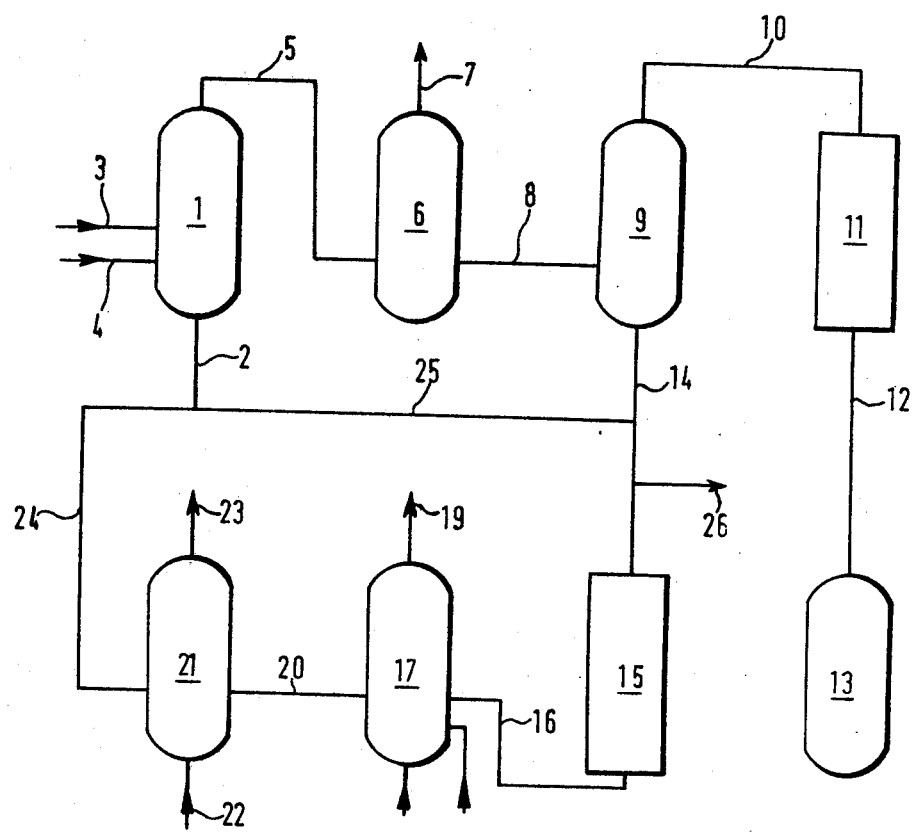

REACTIVATION OF SPENT COPPER CONTAINING HYDROCYANATION CATALYSTS

REACTIVATION OF SPENT CATALYSTS

THIS INVENTION relates to the reactivation of spent catalysts, more particularly to the reactivation of spent hydrocyanation catalysts and to the use of the reactivated catalysts in hydrocyanation reactions.

It has been proposed to carry out hydrocyanation reactions in the presence of copper salts as catalysts. More particularly it has been proposed to manufacture organic nitriles by reacting an olefin or a diolefin with hydrogen cyanide in the presence of a copper halide catalyst. A particularly suitable copper halide catalyst for use in this reaction is that in which the copper halide is in the form of a complex with an organic nitrile as described, for example, in United Kingdom Pat. No. 1,429,651. The use of copper halide catalysts in this reaction is also described in United Kingdom Pat. Nos. 1,429,169 and 1,482,909.

A particular example of the hydrocyanation reactions mentioned in the preceding paragraph, which may serve for the purposes of illustration, is the reaction of butadiene with hydrogen cyanide in the presence of the complex of a cuprous halide and an organic nitrile as catalyst to give 3-pentenenitrile as the principal product. Although a wide choice of nitriles for forming the complex with the cuprous halide is available (as set out, for example in United Kingdom Pat. No. 1,429,651), a particularly suitable nitrile for convenience in operating the process is adiponitrile, as described in our copending United Kingdom Patent Application No. 12916/77.

During this, and related, hydrocyanation reactions, the copper halide catalyst gradually becomes inactive or spent. We have now found that the spent catalyst can be reactivated by treating it with hydrogen halide.

Accordingly our invention provides a process for the reactivation of an at least partially spent copper halide hydrocyanation catalyst which comprises treating the said spent catalyst with hydrogen halide.

Although we do not wish to be bound by theory, we consider that a cuprous halide/nitrile complex, which, as we have already mentioned, is particularly suitable for use in hydrocyanation reactions, is represented by the formula R C N Cu X, when RCN is the nitrile and X a halide. Where the nitrile is adiponitrile we consider that the active catalyst is represented by the formula A D N Cu X where ADN represents the molecule of adiponitrile. The compound represented by that formula (where X=Cl) may be obtained by dissolving cuprous chloride in hot adiponitrile and cooling when the solid product separates. It has the same infra-red spectrum in adiponitrile as copper chloride in adiponitrile, and has the same catalytic activity in the reaction of butadiene and hydrogen cyanide in adiponitrile as has cuprous chloride.

During the reaction of butadiene and hydrogen cyanide in the presence of a cuprous halide catalyst and adiponitrile there is a growth of two bands in the infra-red spectrum at $2120\ cm^{-1}$ and $2110\ cm^{-1}$, and eventually a compound starts to separate after many hours which is characterised by the same two bands and is identical with the compound represented by the formula A D N $(Cu\ CN)_2$ which may be obtained by dissolving cuprous cyanide in hot adiponitrile and cooling (see Example 1). This compound has no catalytic activity in the reaction of butadiene and hydrogen cyanide and is considered to be identical with the spent catalyst which is generated in the reaction of butadiene and hydrogen cyanide in the presence of a cuprous halide catalyst and adiponitrile.

In the reactivation process of our invention the halide is preferably chloride, bromide or iodide, more preferably chloride or bromide.

The amount of hydrogen halide used in the reactivation is preferably at least 1 g. mole for each g. atom of copper in the spent catalyst. An excess of hydrogen halide over this amount, for example up to 100% excess may be used, but there is no value in using much larger excesses than this since they are wasteful and may lead to a reduction in the activity of the reactivated catalyst.

The hydrogen halide is preferably used in anhydrous form, therefore conveniently in gaseous form.

The reactivation treatment is conveniently carried out at ambient temperature, e.g. at 5° to 25° C., but temperatures outside this range may be used, e.g. from $-50°$ C. to $+100°$ C. preferably from $-50°$ C. to 50° C. The reactivation reaction is fairly rapid and times of treatment are, for example, for 0.5 minutes to 30 minutes.

The reactivation treatment is preferably carried out in solution or in suspension in a suitable liquid. After the treatment it may be desirable to remove any excess hydrogen halide present by purging the liquid with a suitable inert gas, for example nitrogen.

The spent catalyst may be isolated from a hydrocyanation reaction mixture, e.g. by filtration, prior to reactivation. When so isolated it is dissolved or suspended in a liquid for treatment with hydrogen halide. Suitable liquids are nitriles, hydrocarbons, e.g. benzene, toluene and xylene, and chlorinated hydrocarbons, e.g. chloroform, carbon tetrachloride, tetrachloroethylene and chlorobenzene. Where the reactivated catalyst is to be recycled for re-use in the hydrocyanation reaction from which the spent catalyst was obtained, the liquid for the reactivation step is preferably the solvent used in the hydrocyanation reaction, e.g. adiponitrile.

The spent catalyst does not have to be isolated prior to reactivation, however, and, if desired, the reactivation process can be applied to the spent catalyst in the total hydrocyanation reaction mixture. Preferably, however, the hydrogen cyanide, the compound being hydrocyanated, e.g. the olefin or diolefin, and the hydrocyanation product, usually a nitrile, are first isolated from the hydrocyanation reaction mixture, and the spent catalyst in the solvent is then subjected to treatment with hydrogen halide. The solvent containing the reactivated catalyst is then recycled for re-use in the hydrocyanation reaction.

The spent catalyst does not have to be separated from still active catalyst, and the reactivation process may be applied to partially spent catalyst. Moreover, where a reactor stream containing spent catalyst is separated for recycle, a part only of that stream may be subjected to the reactivation process.

The reactivation process of our invention is particularly adapted for use in continuous hydrocyanation reactions. Such use is illustrated in the drawing which is a diagramatic representation of a plant for the manufacture of 3-pentenenitrile by hydrocyanation of butadiene in the presence of a cuprous chloride catalyst in adiponitrile. In the drawing 1 is a reactor, 2 is a conduit through which a solution of cuprous chloride catalyst in adiponitrile is introduced into the reactor, 3 and 4 are conduits for introducing hydrogen cyanide and butadiene respectively into the reactor, 5 is a conduit for leading the reaction mixture to a first still 6 in which excess hydrogen cyanide and butadiene are removed as vapour via connection 7 to a recovery system, 8 is a conduit leading the residue of the first distillation to a second still 9 in which the product 3-pentenenitrile is distilled and the vapour led via a conduit 10 to a condenser 11 and thence via a conduit 12 to a product storage vessel 13, 14 is a conduit leading the residue of adiponitrile and catalyst to a cooler 15 and thence via a conduit 16 to the catalyst reactivation vessel 17 into which dry hydrogen chloride is introduced via conduit 18 and from which excess gas is removed to a recovery system via conduit 19, 20 is a conduit for leading the reactivated catalyst solution to the hydrogen chloride purge vessel 21 into which nitrogen is introduced via conduit 22 and from which gas is removed via conduit 23 to a waste gas treatment system, 24 is a conduit leading the nitrogen-purged reactivated catalyst solution to the inlet 2 to the reactor, 25 is a conduit leading the residue of adiponitrile and catalyst from the still 9 to the inlet 2 to the reactor and by-passing the catalyst reactivation system, 26 is a conduit for removing a catalyst solution purge and 27 is a conduit for introducing make-up catalyst solution. In operation the proportion of catalyst solution by-passing the catalyst reactivation system via conduit 25 is adjusted as necessary to maintain the catalyst activity in the reactor 1 at an appropriate level.

We find in some instances that the reactivated catalyst has greater activity than freshly prepared catalyst.

3-Pentenenitrile is particularly valuable for further reaction with hydrogen cyanide in the presence of a catalyst to give adiponitrile. Adiponitrile may be hydrogenated to hexamethylene diamine, a valuable intermediate for polycondensation with dicarboxylic acids to give polyamides, especially, for example, with adipic acid to give polyhexamethylene adipamide (nylon 6,6) a well-known polyamide for the manufacture of fibres, films and mouldings.

In the hydrocyanation of butandiene using cuprous halide catalysts the proportion of linear 3-pentenenitrile, directly convertible to adiponitrile, which is produced in relation to branced methylbutene nitrile, which is not so directly convertible, is at least 4:1 and may be appreciably higher.

The invention is illustrated but not limited by the following Examples:

EXAMPLES 1 to 6

The adiponitrile bis copper (1) cyanide complex of formula A D N (Cu CN)$_2$ was prepared in the following manner:

Copper (1) cyanide (2 g) and adiponitrile (10 ml) were stirred under nitrogen at 150°–155° C. for 2 hours. A clear solution was formed and was quickly cooled. The complex precipitated as an off-white solid. The product was filtered, washed with methanol and dried. Yield 2.7 g.

Analysis-Found %C 33.3, %H 2.7, %N 19.7; $C_8H_8N_4Cu_2$ requires %C 33.4, %H 2.8, %N 19.5. The compound shows two bands in the infra-red spectrum at 2120 cm$^{-1}$ and 2110 cm$^{-1}$.

A solution of the complex A D N (Cu CN)$_2$ (0.87 g) in adiponitrile (4 ml) was purged with nitrogen in a Fischer and Porter tube for 10 minutes at 20° C. Dry hydrogen chloride was then passed through the solution at a rate of 50 ml/min for the time indicated in the following Table 1. The tube was then cooled to −40° C. and liquid butadiene (10 ml) and liquid hydrogen cyanide (5 ml) added. The tube was then sealed and heated for 12 hours at the temperature indicated in Table 1. After cooling, the tube was opened and the contents analysed by gas-liquid chromatography. For comparison, the experiments were repeated using cuprous chloride (0.6 g) in adiponitrile (40 ml) instead of the reactivated A D N (Cu CN)$_2$ complex. The results are given in Table 1.

TABLE 1

| Example No. | Catalyst | Time of Passage of HCl (min) | Reaction Temp °C. | Product (Total Mononitriles) (g) | % Conversion of Butadiene |
|---|---|---|---|---|---|
| 1 | ADN(CuCN)$_2$ | 5 | 110–115 | 6.94 | 71.2 |
| Control | CuCl | — | 110–115 | 4.95 | 50.8 |
| 2 | ADN(CuCN)$_2$ | 5 | 100 | 5.32 | 54.5 |
| Control | CuCl | — | 100 | 3.22 | 33.0 |
| 3 | ADN(CuCN)$_2$ | 0.5 | 135 | 6.37 | 65.3 |
| 4 | " | 5.0 | 135 | 6.76 | 69.3 |
| Control | CuCl | — | 135 | 5.05 | 51.8 |
| 5 | ADN(CuCN)$_2$ | 0.5 | 130 | 6.54 | 67.1 |
| 6 | " | 5.0 | 130 | 6.94 | 71.2 |
| Control | CuCl | — | 130 | 4.90 | 50.3 |

EXAMPLES 7 to 12

A solution of the complex A D N (Cu CN)$_2$ (0.44 g) in adiponitrile (4 ml) was purged with nitrogen as in the preceding Examples and dry hydrogen chloride passed through the solution at a rate of 20 ml/min for the time indicated in the following Table 2. The tube was then cooled to −40° C. and liquid butadiene (3.25 g) and liquid hydrogen cyanide (1.7 g) added. The tube was then sealed and heated for 16 hours at 100° C. The tube was then opened and the contents anaylsed as in the preceding Examples. For comparison an experiment was carried out under the same conditions using cuprous chloride (0.6 g) in adiponitrile (4 ml) instead of the reactivated A D N (Cu CN)$_2$ complex. The results are given in Table 2.

TABLE 2

| Example No. | Catalyst | Time of Passage of HCl (mins) | Product (Total Mononitriles) (g) | Ratio 3PN*/2M3BN | % Conversion of Butadiene |
|---|---|---|---|---|---|
| 7 | ADN(CuCN)$_2$ | 0.5 | 0.11 | 10 | 2.3 |
| 8 | " | 1.0 | 0.16 | 15 | 3.3 |
| 9 | " | 2.0 | 1.54 | 21 | 31.6 |
| 10 | " | 4.0 | 2.61 | 15.3 | 53.5 |
| 11 | " | 6.0 | 2.28 | 21.8 | 47.8 |
| 12 | " | 12.0 | 1.84 | 29.7 | 37.7 |
| Control | CuCl | — | 1.28 | 13.2 | 26.3 |

*3PN = 3-pentenenitrile
2M3BN = 2-methyl-3-butenenitrile

EXAMPLE 13

A glass pressure tube was purged with nitrogen, cooled to −40° C., then charged with copper (1) chloride (0.6 g), adiponitrile (4 ml), butadiene (10 ml; liquid) and anhydrous hydrogen cyanide (5 ml). The tube sealed and heated at 130° C. with magnetic stirring for 12 hours. The tube was cooled to −40° C., opened and excess hydrogen cyanide and butadiene swept out with nitrogen. The product was anaylsed by GLC and contained 4.04 g of mononitrile, a 41.5% conversion of butadiene. The mononitriles were flash-distilled and the catalyst solution purged with dry hydrogen chloride (20 ml. min$^{-1}$) for 2 minutes. The catalyst solution was then returned to the reaction tube, purged with nitrogen, cooled to −40° C. and butadiene (10 ml) and anhydrous hydrogen cyanide (5 ml) added. The tube sealed and heated at 130° C. with magnetic stirring for 12 hours. The product was worked up as above and shown to contain 7.62 g of mononitriles (78.2% butadiene conversion).

I claim:

1. A process for the reactivation of an at least partially deactivated copper halide catalyst in a nitrile solvent, said catalyst having been deactivated in a process for hydrocyanation of butadiene with hydrogen cyanide in a nitrile solvent in the presence of a copper halide catalyst, which comprises;

(a) isolating hydrogen cyanide, butadiene and 3-pentenitrile from the hydrocyanation reaction mixture and collecting a reaction mixture residue comprising said nitrile solvent and catalyst and;

(b) treating said reaction mixture residue with hydrogen halide in an amount sufficient to reactivate said catalyst for re-use in said hydrocyanation reaction.

2. A process according to claim 1 in which the hydrogen halide is hydrogen chloride or hydrogen bromide.

3. A process according to claim 1 in which the amount of hydrogen halide used in the reactivation is at least 1 g. mole for each g. atom of copper in the spent catalyst.

4. A process according to claim 3 in which the amount of hydrogen halide used in the reactivation is up to 100% excess of 1 g. mole for each g. atom of copper in the spent catalyst.

5. A process according to claim 1 in which the reactivation treatment is carried out at a temperature in the range −50° C. to +100° C.

6. A process according to claim 1 in which the time of the reactivation treatment is from 0.5 minutes to 30 minutes.

7. A process according to claim 1 in which the nitrile solvent comprises adiponitrile.

* * * * *